US 8,364,408 B2

(12) United States Patent
Srinivasa

(10) Patent No.: US 8,364,408 B2
(45) Date of Patent: Jan. 29, 2013

(54) GLOBAL ALIGNMENT OF SEQUENCE DATA

(75) Inventor: Deepak M. Srinivasa, Bangalore (IN)

(73) Assignee: International Business Machines Corporation, Armonk, NY (US)

( * ) Notice: Subject to any disclaimer, the term of this patent is extended or adjusted under 35 U.S.C. 154(b) by 1605 days.

(21) Appl. No.: 11/214,603

(22) Filed: Aug. 30, 2005

(65) Prior Publication Data

US 2007/0048730 A1    Mar. 1, 2007

(51) Int. Cl.
G01N 33/48    (2006.01)
G06G 7/48    (2006.01)

(52) U.S. Cl. ............................................ 702/19; 703/11
(58) Field of Classification Search .................. None
See application file for complete search history.

(56) References Cited

U.S. PATENT DOCUMENTS

2004/0126840 A1*  7/2004  Cheng et al. .................. 435/69.1

OTHER PUBLICATIONS

Brudno et al., Fast and sensitive multiple alignment of large genomic sequences, BMC Bioinformatics, 2003, 4(66), 1-11.*
Brudno et al. (Genome Research, 2003, 13, 721-731), referred to as (Brudno LAGAN).*
Gusfield, D. "Algorithms on strings, trees, and sequences: Computer Science and Computational Biology", section 12.2.3, 1997, Cambridge Publishers.
S. B. Needleman and C. D. Wunsch, "A general method applicable to the search of similarities in the amino acid sequence of two proteins", *Journal of Molecular Biology*, 1970, pp. 443 to 453, vol. 48.
Chang, W. I. and Lampe, J., "Theoretical and empirical comparisons of approximate string matching algorithms", *Proceedings of the 3rd Symposium on Combinatorial Pattern Matching*, 1992, Springer LNCS 644, pp. 175 to 184.
Peltola M., Soderlund H., Tarhio J., and Ukkonen E., "Algorithms for some string matching problems arising in molecular genetics". *Proceeding of the 9th IFIP World Computer Congress*, 1983, pp. 59 to 64.

* cited by examiner

*Primary Examiner* — Larry D Riggs, II
(74) *Attorney, Agent, or Firm* — Geroge R. McGuire; David B. Woycechowsky; Bond Schoeneck & King

(57) ABSTRACT

To determine optimal alignment of two molecules, an alignment space of two strings representing element sequences of the molecules is conceived as a grid of cells, where each cell represents alignments between substrings of the two strings. The cells are tested against conditions that are framed, in the context of the (wh)-density global alignment problem. Two such conditions do not require an examination of the actual characters of the strings, and are hence computed with relative speed. A third condition, which involves examination of the characters in the string further prunes the cells that are to be considered.

2 Claims, 4 Drawing Sheets

GLOBAL ALIGNMENT OF SEQUENCE DATA

FIELD OF THE INVENTION

The present invention relates to global alignment of molecular sequences, and relates more particularly to a solution to a (wh)-density problem, defined herein, for the alignment of data representing such sequences.

BACKGROUND

A pairwise global alignment problem was defined by S. B. Needleman and C. D. Wunsch, "A general method applicable to the search of similarities in the amino acid sequence of two proteins," *Journal of Molecular Biology*, 1970, pages 443-53, volume 48) ("*Needleman and Wunsch*"), which is hereby incorporated herein by reference in its entirety. Needlemen and Wunsch provide a dynamic programming (DP) approach to the global alignment problem, as follows. Given two strings $S_1$ and $S_2$ representing respective molecular sequences, a global alignment A between $S_1$ and $S_2$ is obtained by first inserting chosen spaces (or dashes), either into or at the ends of strings $S_1$ and $S_2$, and then placing the two resulting strings one above the other so that every character or space in either string is opposite to a unique character, or a unique string in the other string. (Note that possible alignments include alignments in which no spaces are inserted in either string, no space is inserted in one string and one space is inserted in the other string, or vice versa, and in which one space is inserted in each string.)

An example is given with reference to Table 1 below. If $S_1$="cacdbd" and $S_2$="cabbdb", $S_1$ and $S_2$ are aligned with an alignment A given in Table 1 below.

TABLE 1

| $S_1'$ | c | a | c | — | d | b | d |
|---|---|---|---|---|---|---|---|
| $S_2'$ | c | a | b | b | d | b | — |
| Position i | 1 | 2 | 3 | 4 | 5 | 6 | 7 |

The i-th character of $S_1'$ or $S_2'$ in Table 1 above is in position i of the alignment A. Of all the alignments that are possible between two strings $S_1$ and $S_2$, the alignment that maximizes the matches between characters in corresponding positions of the respective strings is referred to as an optimal alignment.

The global alignment problem, as defined in *Needleman and Wunsch*, and paraphrased above, deals with the computation of all possible optimal alignments between two strings $S_1$ and $S_2$.

A variation of the global alignment problem is the k-difference global alignment problem. The k-difference global alignment problem deals with the computation of all optimal alignments between two strings $S_1$ and $S_2$, such that the number of mismatches in the reported alignment is at most k. The k-difference global alignment problem is described in section 12.2.3 of Gusfield, D., "Algorithms on strings, trees, and sequences: Computer Science and Computational Biology," 1997, Cambridge Publishers, which is hereby incorporated by reference in its entirety.

Global alignment criteria have application in various fields. One particular area concerns sequencing biological data. Existing computational techniques associated with alignment problems are not wholly adequate for such biological applications. A need consequently exists for improved computational techniques suitable for use in biological applications.

SUMMARY

A constrained version of the pairwise global alignment problem, termed the (wh)-density global alignment problem, is defined herein and a computational solution is also described.

An alignment space of two strings is conceived as a grid of cells representing partial alignments between the strings. The cells are tested against at least one initialization condition that does not require an examination of the actual characters of the strings, and is hence computed with relative speed. Cells that fail the at least one initialization condition are discarded from further consideration. An extension condition, which involves examination of the characters in the strings, further prunes the cells that are to be considered. This third condition is only applied to cells not eliminated by application of the initialization condition. The solution to the (wh)-density global alignment problem is thus obtained by a computation that involves only the cells that have passed all the previous conditions.

As a result of imposing the necessary conditions on the cells of the grid, a portion of the grid is eliminated from computation, thereby achieving relative efficiency. In addition, the technique described herein ensures that all and only the optimal solutions to the (wh)-density global alignment problem are computed in a final step.

As the density constraint becomes more stringent, more cells are eliminated from dynamic programming computations. Typically, a majority of the above mentioned cells is not examined. The expected running time of the computations in this case is correspondingly reduced.

DETAILED DESCRIPTION

Figure 1:
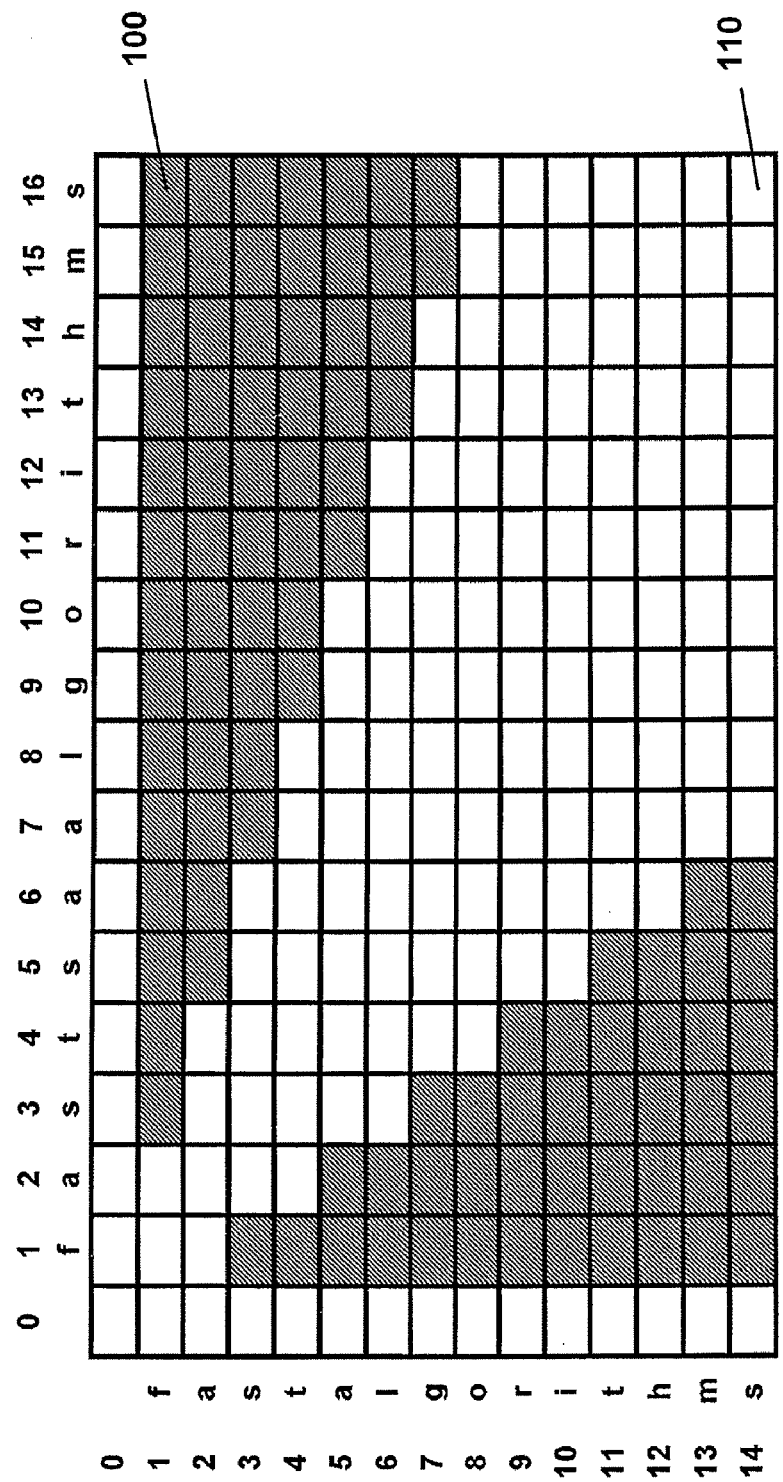
FIG. 1 is a schematic representation of cells in a global alignment example for w=2, h=1, n=14 and m=16. Hatched cells fail a first necessary condition, while unhatched cells meet this first necessary condition.

The pairwise global alignment technique described herein is first defined as a problem. A computational framework is then described, with reference to first, second and third necessary conditions against which successful alignments are matched. The first and second described necessary conditions are not sufficient. The third described condition, together with the computation of a "traceback" step, as later described, act as a necessary and sufficient condition to complete computations. A data structure suited for computational analysis is described in the context of a computational example.

Problem Definition

The (wh)-density global alignment problem is defined as follows. The (wh)-density global alignment problem is similar to the k-difference problem described above. The following definitions formally state the (wh)-density problem. A global alignment A between two strings $S_1$ and $S_2$ satisfies the (wh)-density constraint if any consecutive "w" alignment positions of A has at least "h" matches. Such an alignment is referred to as a (wh)-density global alignment.

An example problem is presented in relation to Table 2 below to illustrate what is meant by "alignment" and "alignment position." Let $S_1$="fastsaalgorithms" and $S_2$="fastalgorithms". Let w=2 and h=1. This combination of w and h, in a (wh)-density global alignment constraint specifies that for every two consecutive positions (w=2) in one of the strings at least one of the positions (h=1) must match the corresponding position in the other string. Two possible alignments, $A_1$ and $A_2$, are presented in Table 2 below.

TABLE 2

| Alignment $A_1$ | | | | | | | | | | | | | | | |
|---|---|---|---|---|---|---|---|---|---|---|---|---|---|---|---|
| $S_1$ | f | a | s | t | s | a | a | l | g | o | r | i | t | h | m | s |
| $S_2$ | f | a | s | t | — | — | a | l | g | o | r | i | t | h | m | s |
| Alignment $A_2$ | | | | | | | | | | | | | | | |
| $S_1$ | f | a | s | t | s | a | a | l | g | o | r | i | t | h | m | s |
| $S_2$ | f | a | s | t | — | a | — | l | g | o | r | i | t | h | m | s |

The above examples serve to illustrate the meaning of the term "alignment position" as it is used herein, and to contrast its meaning to the term "character." In Alignment $A_1$ above, the character "f" is the first alignment position for both strings $S_1$ and $S_2$, and the character "l" is the eighth, for example. Note that the position of a character in a string depends on the alignment of the string. For example, the second "a" in string $S_2$ is in the seventh alignment position for alignment $A_1$ and in the sixth alignment position for alignment $A_2$ above. Note also that a position in a string may not always be a character. For example, the sixth position in string $S_2$ for alignment $A_1$ is a blank, i.e., non-character. Furthermore, "alignment position" is also appropriate because certain operations are described herein that are carried out based on alignment position independently of the identity of string characters (or non-characters).

In the example of Table 2, Alignment $A_1$ does not satisfy the density constraint because "s" and "a" are two consecutive positions of $S_1$, and there is no match with the corresponding position of $S_2$ for either of these positions of $S_1$. $A_2$ does satisfy the density constraint. Therefore, $A_2$ is a (wh)-density global alignment for w=2 and h=1, while $A_1$ is not.

The (wh)-density optimal global alignment A, given two strings $S_1$ and $S_2$, is the alignment of the strings that not only satisfies the (wh)-density global alignment constraint, as explained in the above example, but that also maximizes an alignment score of the strings. The alignment score (also referred to herein as "alignment value") is merely a count of the number of matching positions of the strings. Note that in the above example, alignments $A_1$ and $A_2$ have the same alignment score, even though only $A_2$ satisfies the (wh)-density global alignment constraint.

Original Technique

The original dynamic programming technique of *Needleman and Wunsch* is briefly explained to set the context for a description of how one or more solutions are computed for the (wh)-density global alignment problem defined herein.

Two strings are given as input, $S_1$ of length m and $S_2$ of length n. A grid of cells (m×n) is created to represent numerous possible alignments among portions of these two strings $S_1$ and $S_2$. In particular, each cell in this grid represents a partial alignment between the two input strings and each cell has a particular value that is referred to herein as an "optimal alignment score," or simply "alignment score." For example, cell (i, j) in this grid (with i≦m and j≦n) represents a partial alignment between the substrings $S_1[1 \ldots i]$ and $S_2[1 \ldots j]$, where substring $S_1[1 \ldots i]$ is the first i characters in string $S_1$, and substring $S_2[1 \ldots j]$ is the first j characters of string $S_2$. The value of cell (i, j) is based on alignment scores of all the possible alignments between substrings $S_1[1 \ldots i]$ and $S_2[1 \ldots j]$. That is, scores are computed for each possible alignment of the substrings $S_1[1 \ldots i]$ and $S_2[1 \ldots j]$, and cell (i, j) in the grid is assigned the best score among all of the alignment scores. Note that more than one of the alignments may have the same alignment score, so that cell (i,j) does not necessarily correspond to any one particular one of the alignments. Note also, the last cell (m, n) in the grid indicates the optimal alignment score for the entirety of the two strings $S_1$ and $S_2$.

An alignment score may be computed, for example, by adding up the number of matching alignment positions for two strings or substrings in a given alignment. Alternatively, a first weight may be assigned for matching alignment positions in a given alignment; a second weight may be assigned for non-matching alignment positions; the number of matching positions may be multiplied by the first weight, yielding a first weight-adjusted sum; the number of non-matching positions may be multiplied by the second weight, yielding a second weight-adjusted sum; and the two weight-adjusted sums may be added to yield the score for the alignment.

Values for the cells of the grid are computed in a particular sequence. This is because the alignment score for a cell may be determined by incremental computation from its adjacent cells. (The adjacent cells for a cell are those that are above, to the left and diagonally above and left.) Initially alignment scores are determined for the cells of the first row and first column in the grid. Then numerical values are determined in sequence for the rest of the cells in the grid. That is, after the cells of the first row and first column have numbers in them representing their respective optimal alignment scores, alignment scores are determined for all the remaining cells of the grid in a row-by-row fashion, starting with the second cell of the second row, and so on, until finally an optimal alignment value is determined for the last cell (m, n), which indicates the optimal alignment score for the entirety of the two strings $S_1$ and $S_2$.

The alignment values assigned to the cells of the grid give rise to back pointers. That is, except for cell (0, 0), all the other cells have back pointers associated with them. The back pointers are also determined in sequence. During initialization, the cells of the first row each have a back pointer established to the cell that is to their left. Similarly, the cells of the first column each have a back pointer established to the cell above. The optimal alignment score is determined for a new cell in the sequence by derivation from at least one of the earlier cells, and one or more back pointers are accordingly established from the new cell to the one or more earlier cells. That is, more than one cell may lead to the optimal alignment score for an adjacent cell. In this case, back pointers are established to all such adjacent cells. Since there are three cells adjacent to each cell in the grid (aside from cells in the first row and column), each cell might have one, two or three back pointers.

Once alignment scores are determined for each cell and the final cell (m, n) is reached, as described above, this concludes forward computation. At this stage, the optimal alignment value for the two strings has been computed and the optimization problem is thus complete. However, the actual alignments are yet to be collected. This is when a traceback step begins. Once back pointers are established, these back pointers can be traced back starting from the "last" cell (m, n) back through the grid to the "first" cell (0, 0). Since every cell has at least one back pointer, there is at least one route from the last cell (m, n) to the first cell (0, 0). Some cells might have more than one back pointer. This leads to choices at these cells, and multiple solutions for the same two strings, i.e., multiple alignments that represent the same optimal alignment value. Every path from the cell (m, n) to cell (0, 0) through the back pointers is a unique solution to the problem. The trace back step collects all such alignments, and reports these alignments as solutions to the given problem instance.

Overview of an Embodiment of the Present Invention

The original dynamic programming technique of *Needleman and Wunsch* finds optimal alignments between two given strings. The techniques described herein are applied to a similar problem but with a further constraint, namely the (wh)-density constraint. According to an embodiment of the present invention, a number of steps are performed that are different than or in addition to the teachings of *Needleman and Wunsch* to cater to this further constraint that the reported alignments have h matches in every consecutive w alignment positions, and that these reported alignments are optimal.

Specifically, a grid of cells is first constructed for respective substrings of two strings, as described above, and some of the cells are eliminated from further consideration without even looking at individual characters of the strings. This can be determined by just looking at the positions of the cells in the grid with respect to the string values of m, n, and the selected parameters of w and h relating to the (wh)-density constraint. Such cells are identified and eliminated by using the first and second necessary conditions, as described below, which may be referred to herein as conditions of a "initialization" condition.

Once these unfeasible cells are eliminated from further consideration, a subset of the grid cells remains for subsequent dynamic programming computation. Eliminating cells by applying the initialization conditions described above provides advantages as dynamic programming computations need not be performed for the eliminated cells.

Next, the additional (wh)-density constraint is tracked using data structures described below as w-frames. Tracking is achieved by associating each cell with a w-frame, in addition to use of the optimal number taught by *Needleman and Wunsch*. Using this w-frame for every cell, a determination is made as to whether or not the density constraint is met. This is referred to herein as a "feasibility step", and corresponds directly with the third necessary condition described below. Since the third necessary condition relates to adjacency of cells remaining after application of the above described "initialization" conditions, the third necessary condition may be referred to herein as an "extension" condition. If found to be infeasible, no back pointers are established. Each cell is processed in a row-by-row fashion, until the last cell (m, n).

At least one solution exists to the given problem instance if a back pointer is established in cell (m, n). It may so happen sometimes that for the given two strings, no solution satisfies the given density constraint. In that case, a back pointer in the last cell cannot be established at all.

As with the dynamic programming technique of *Needleman and Wunsch*, after the forward computations, the optimality value must be computed for the last cell. However, the alignments are yet to be collected. According to an embodiment of the invention, the solution alignments are collected just like in the teachings of *Needleman and Wunsch*, but with a difference.

The conditions that are established according to the herein described embodiment of the invention ensure that if there is a back pointer established in a cell, then there is at least one path from there to the cell (0, 0) that meets the density constraint. While there is at least one path that meets the density constraint, not every path from a cell that has a back pointer to cell (0, 0) is necessarily a solution. Accordingly, unlike the teachings of *Needleman and Wunsch*, one cannot just run through all paths from cell (m, n) to cell (0, 0) through the back pointers and report these paths as solutions.

Instead, a further check is needed while tracing back and collecting alignments. The density constraints are checked again. The w-frames have already been computed for each of these cells during the forward computation. This is the traceback condition referred to herein that one checks. If the cell satisfies this condition, then that route can be safely taken. Solution alignments are collected in this manner, and reported to the user.

Computational Framework

A grid of cells is used to facilitate computations solving the above-described problem for any particular example. FIGS. 1 to 4 schematically represent such notional grids, and are described in further detail below.

The first and second necessary conditions, described below, are both necessary though not sufficient conditions. That is, alignments not satisfying these conditions are infeasible alignments, but there is no guarantee that alignments satisfying these conditions are feasible solutions. The third necessary condition is imposed in conjunction with a traceback step described below. The first and second necessary conditions eliminate a substantial portion of the alignment grid preliminary to the final computational stage.

First Necessary Condition

A first necessary condition for an alignment A to be feasible is now described. The following principle leads to the first necessary condition.

Principle 1: An alignment A of length p, $p \geq w$, has at least hp/w matches in order to meet the density constraint of h matches in any w consecutive alignment positions.

Proof: This proof is an application of the pigeonhole principle. Divide the alignment A into non-overlapping p/w units each of length w. There may be a residual unit of length less than w, but a minimum bound is set on the number of matches required. Each of these p/w units has at least h matches, since each unit is of length w. Therefore the minimum number of matches in A should be hp/w (since the units are non-overlapping).

Using Principle 1, an embodiment of the present invention provides a first necessary condition for deciding whether a cell (i, j) is to be considered for dynamic programming computation. Observe that the criteria for a path meeting the density constraint are minimum possible alignment length and maximum possible matches. If the path that can do best in terms of the density constraint itself fails to meet the density constraint, then there is no possibility of other paths from that cell meeting the specified density constraint. This is the rationale of the following condition.

For cell (i, j), the minimum possible alignment length is max(i, j), i.e., the larger value of the two values i and j, and the maximum possible matches is min(i, j), i.e., the smaller value of the two values i and j. Therefore one arrives at the following first necessary condition for a cell (i, j) to be considered for dynamic programming computation, which follows from Principle 1. This necessary condition is expressed below as Equation [1].

$$\min(i,j) \geq \max(i,j) \cdot (h/w) \text{ when } \max(i,j) \geq w \quad [1]$$

Second Necessary Condition

A second necessary condition for an alignment A to be feasible is now described. Observe that the 0-th row and the 0-th column cells trivially satisfy the first necessary condition, expressed in Equation [1] above. Another, second necessary condition can be derived for application to cells in the 0-th row and the 0-th column. The following principle leads to this second necessary condition.

Principle 2: Any alignment A satisfying the (wh)-density constraint cannot have (w−h+1) consecutive mismatches.

Proof: For w−h+1 consecutive mismatches, one can always consider w consecutive alignment positions starting from the beginning of these w−h+1 consecutive mismatches. Since, in such a case, the maximum number of matches possible in those w consecutive positions is h−1, the (wh)-density constraint is inevitably violated.

A cell (i, 0) represents an alignment between $S_1[1 \ldots i]$ and the empty string (because j is 0, no characters from $S_2$ are considered for alignment). The only way to align these two strings is to place spaces below each character of $S_1[1 \ldots i]$. Therefore, an alignment at cell (i, 0) has i consecutive mismatches. Similarly, a cell (0, j) has j consecutive mismatches.

From Principle 2, the following second necessary condition is obtained, expressed below as Equation [2].

if $i=0$, then $j \leq w-h$ if $j=0$, then $i \leq w-h$  [2]

Third Necessary Condition

The third necessary condition involves examining alignments obtained so far. Testing whether or not a cell meets the third necessary condition is "interleaved" with dynamic programming computations. An initialization step is performed once, while iterative computations are performed for cells that meet the first and second necessary conditions.

A feasibility step is performed before each dynamic programming step. This feasibility step is the third necessary condition. So, in each iteration, one first evaluates the third necessary condition, and then performs the dynamic programming step. The next iteration can then be computed.

A cell $(i, j)$ warrants consideration for the dynamic programming computation only if there is at least one alignment between $S_1[1 \ldots i]$ and $S_2[1 \ldots j]$ that meets the density constraint. This is essentially the third necessary condition. The following definition and principle state the third necessary condition more formally.

Definition: For a cell $(i, j)$, the cells $(i-1, j)$, $(i-1, j-1)$ and $(i, j-1)$, if they exist, are called adjacent cells. Let these adjacent cells be respectively denoted by N, NW and W (for North, North West and West).

Principle 3: If none of the alignments extended from of substrings for any of the adjacent cells of adjacent to cell $(i, j)$ have at least h matches in the last w alignment positions, then cell $(i, j)$ need not be considered for the dynamic programming computation, i.e., cell $(i,j)$ does not meet the third necessary condition, referred to herein as an "extension condition."

The term "extending" is used in this context. As previously stated, possible alignments of the strings include alignments in which no spaces are inserted in either string, no space is inserted in one string and one space is inserted in the other string, or vice versa, and in which one space is inserted in each string. For each of these possibilities, an inserted space may be located in any chosen position in its string. In other words, starting from an adjacent alignment position a space may be inserted into one or both strings to shift the alignment of the two strings. Each cell represents a partial alignment. So, moving to cell $(i,j)$ by considering its preceding neighbors, this "extends" the alignment. This is a dynamic programming formulation for global alignment problems.

Proof: Cell $(i, j)$ represents alignments between strings $S_1[1 \ldots i]$ and $S_2[1 \ldots j]$. Let $S_1'$ and $S_2'$ be the strings after a particular choice of spaces inserted in the strings. Consider the last k positions of the strings for all possible alignments between $S_1[1 \ldots i]$ and $S_2[1 \ldots j]$. That is, consider the last alignment position, k, of all alignments between $S_1$ from 1 to i and $S_2$ from 1 to j. That is, consider the last character of each of the strings $S_1$ and $S_2$. There are only three possibilities, which are presented in Table 3 below.

TABLE 3

| | |
|---|---|
| Case 1 | $S_1'(k)$ = space and $S_2'(k) = S_2(j)$ |
| Case 2 | $S_1'(k) = S_1(i)$ and $S_2'(k)$ = space |
| Case 3 | $S_1'(k) = S_1(i)$ and $S_2'(k) = S_2(j)$ |

Case 1 implies that the alignment for cell $(i, j)$ is an extension of the alignment for cell $(i, j-1)$. This extension is realized by establishing a back pointer in cell $(i, j)$ pointing to cell $(i, j-1)$. Case 2 implies that the alignment for cell $(i, j)$ is an extension of the alignment for cell $(i-1, j)$. Case 3 implies that the alignment for cell $(i, j)$ is an extension of the alignment for cell $(i-1, j-1)$. Since there are no other possibilities, each alignment for cell $(i, j)$ is an extension of the alignments of one of the adjacent cells. Therefore, considering only the adjacent cells suffices.

If none of the alignments extended from the adjacent cells have h matches in the last w alignment positions, there is no alignment from cell $(i, j)$ that satisfies the (wh)-density constraint. Therefore, there can be no alignment from that cell $(i, j)$ that can satisfy the (wh)-density constraint. Therefore, cell $(i, j)$ need not be considered for dynamic programming computations.

Computational Examples

Figure 2:
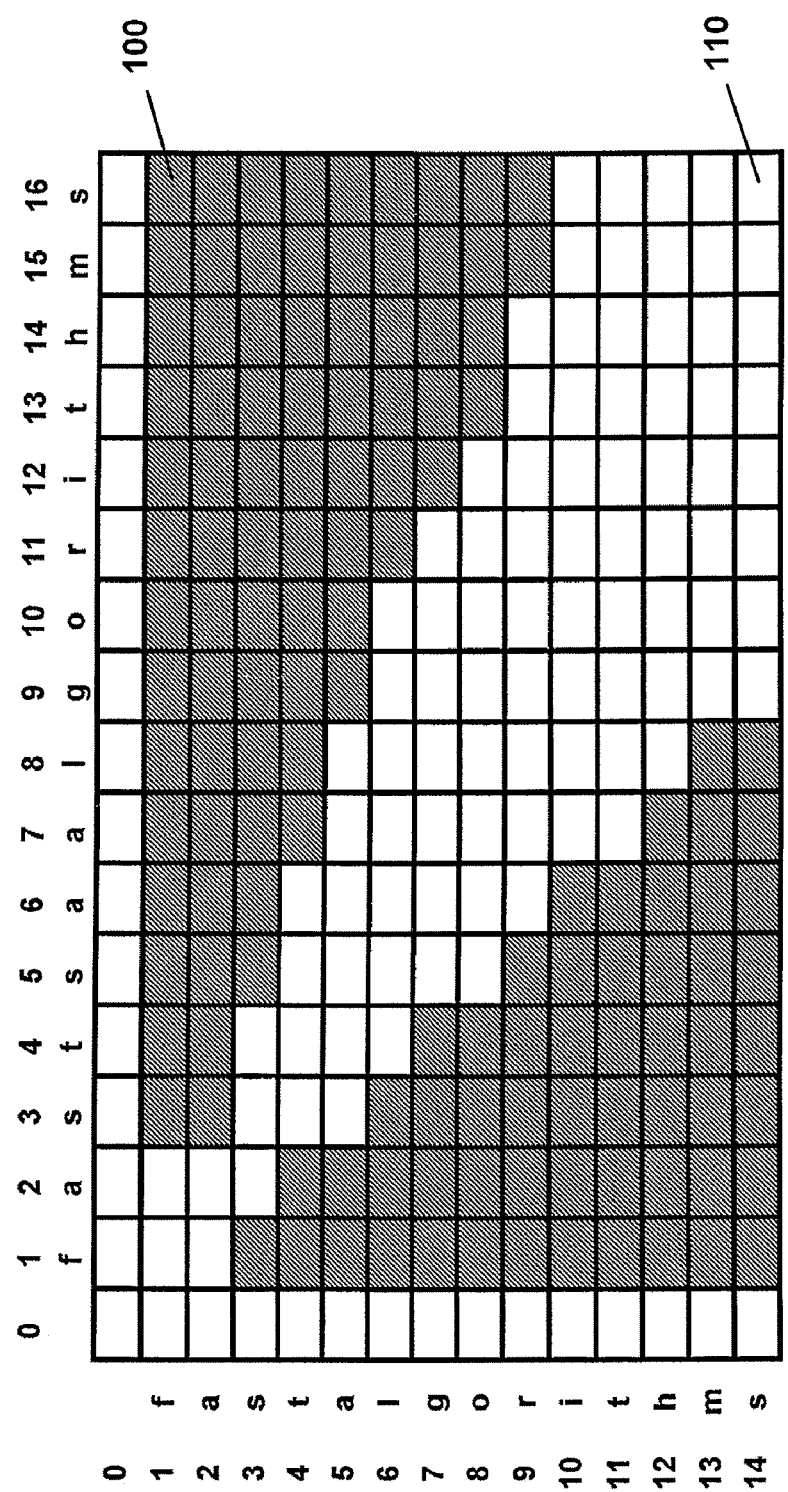
FIG. 2 is a schematic representation of cells in the global alignment example of FIG. 1, but for w=3, and h=2. Hatched cells fail a first necessary condition, while unhatched cells meet this first necessary condition.
Figure 3:
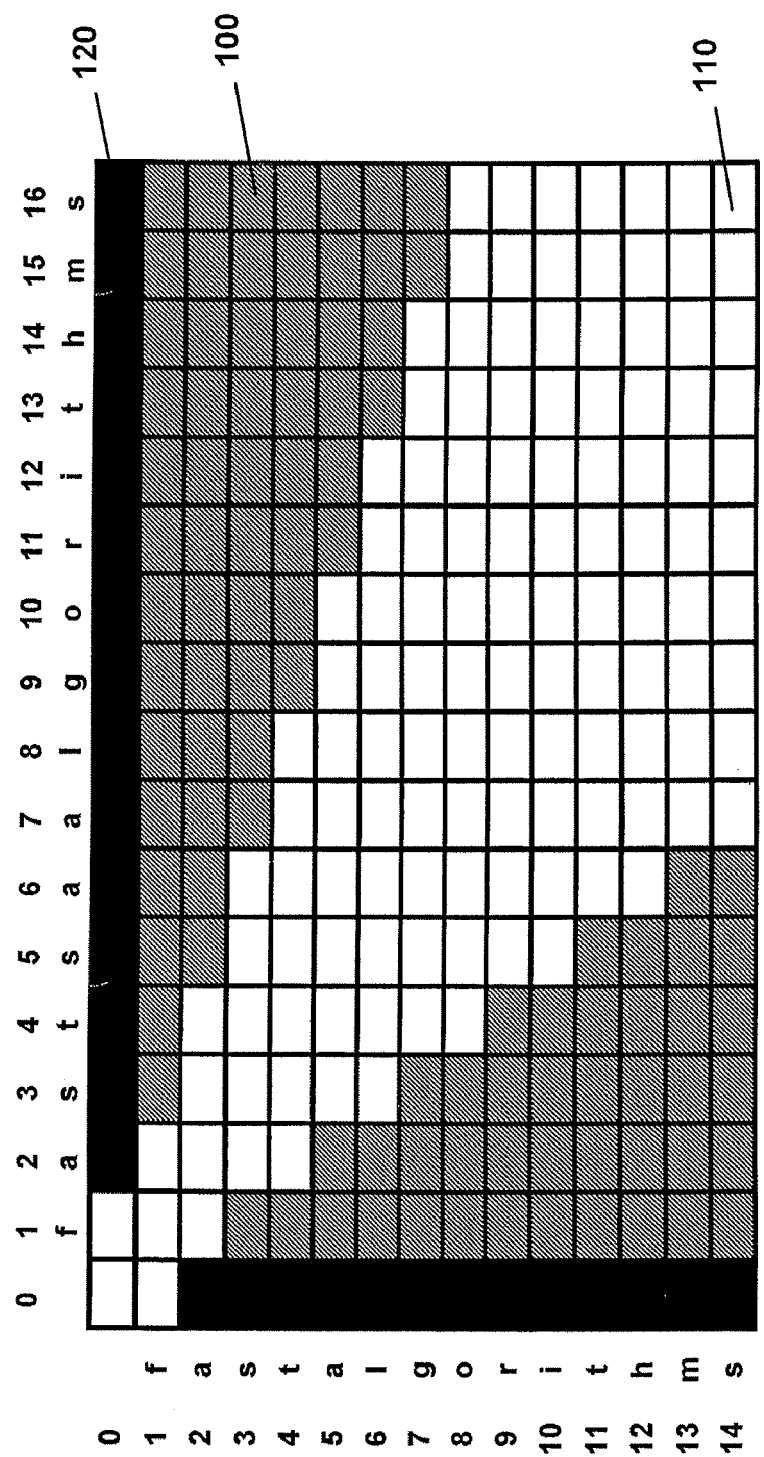
FIG. 3 is a schematic representation of cells corresponding with those of FIG. 1. Hatched cells fail a first necessary condition, and black cells fail a second necessary condition. Unmarked cells meet both first and second necessary conditions, and are candidate cells for meeting the (wh)-density global alignment.

FIGS. 1 to 3 are used to illustrate the following example, which concerns two strings that are of length m=16 and n=14. FIGS. 1 and 2 illustrate use of a first necessary condition.

FIG. 1 illustrates cells that meet or fail the first necessary condition for w=2 and h=1. The hatched cells 100 fail the first necessary condition, and the unmarked cells 110, also called the unhatched cells, meet the first necessary condition and are considered for further computations.

FIG. 2 illustrates the cells that meet or fail the first necessary condition for w=3 and h=2. The hatched cells 100 fail the first necessary condition, and the unmarked cells 110 meet the first necessary condition.

As a first step during the computation of every cell $(i, j)$, the cell is checked to determine whether the cell satisfies the first necessary condition. If the cell satisfies the first necessary condition, then there is a possibility that an alignment between $S_1[1 \ldots i]$ and $S_2[1 \ldots j]$ can satisfy the (wh)-density constraint. If the cell does not satisfy the first necessary condition, then one is assured that there can be no alignment between $S_1[1 \ldots i]$ and $S_2[1 \ldots j]$ that satisfies the (wh)-density constraint. Therefore, the cell $(i, j)$ is not considered for further computation.

FIG. 3 illustrates a grid of cells that meet or fail the second necessary condition. The above-described second necessary condition expressed in Equation [2] is used during the initialization step of the dynamic programming algorithm. FIG. 3 illustrates the same example problem as FIG. 1, but also includes black cells 120 that also fail the second necessary condition.

The algorithm can now proceed only in the regions that are unmarked, namely for those cells that satisfy both the first and the second necessary conditions. These two necessary conditions enable elimination of cells from computations even without examining the two strings that are to be aligned. A "stronger" third described necessary and sufficient condition is derived that requires examining the two input strings.

W-Frame Data Structure

A data structure referred to as a w-frame is used extensively in the algorithm is now described. This w-frame data structure, and two operations using w-frame data structures are defined. A w-frame is associated with a cell $(i, j)$ of the dynamic programming table. The w-frame data structure is used to store information about matches and mismatches in the last w alignment positions of all the feasible alignments discovered between $S_1[1 \ldots i]$ and $S_2[1 \ldots j]$. The information stored in the w-frame is sufficient to decide if a cell $(i, j)$ satisfies the third necessary condition.

Definition: A w-frame is a non-negative integer array of length w. Length w is the same as the w parameter of the (wh)-density constraint. The elements of the w-frame are numbered from left to right, starting from 1 to w. For a w-frame $f$, the value of the element at position i in the w-frame $(1 \leq i \leq w)$, is represented by $f(i)$. Each $f(i)$ is a non-negative integer.

Definition: A unary operation shift defined on a w-frame $f$ is represented as $f.\text{shift}(k)$, where k is a binary number that can take a value of either 0 or 1. This operation returns a w-frame g such that $g(1)=k$ and for $2\leq i\leq w$, $g(i)=f(i-1)+k$.

Definition: A binary operation merge defined on two w-frames $f_1$ and $f_2$, represented as $f_1+f_2$, returns a w-frame $f$ such that for $1\leq i\leq w$, $f(i)=\max(f_1(i), f_2(i))$.

Table 4 below presents an example of $S_1$="fastsaalgorithms" and $S_2$="fastalgorithms". Let w=6 for alignments $A_1$ and $A_2$. The corresponding w-frames of alignments $A_1$ and $A_2$ for i=8 and j=6 are presented in Table 4 below. The derivation of a w-frame for a given alignment and values of i and j is described below Table 4, referring to the examples provided in Table 4.

TABLE 4

| Alignment $A_1$ | f | a | s | t | s | a | a | l | g | o | r | i | t | h | m | s |
| --- | --- | --- | --- | --- | --- | --- | --- | --- | --- | --- | --- | --- | --- | --- | --- | --- |
| | f | a | s | t | — | — | a | l | g | o | r | i | t | h | m | s |
| Position: | 1 | 2 | 3 | 4 | 5 | 6 | 7 | 8 | 9 | 0 | 1 | 2 | 3 | 4 | 5 | 6 |
| w-frame $f_1$ | 1 | 2 | 2 | 2 | 3 | 4 | | | | | | | | | | |
| Alignment $A_2$ | f | a | s | t | s | a | a | l | g | o | r | i | t | h | m | s |
| | f | a | s | t | — | a | — | l | g | o | r | i | t | h | m | s |
| Position | 1 | 2 | 3 | 4 | 5 | 6 | 7 | 8 | 9 | 0 | 1 | 2 | 3 | 4 | 5 | 6 |
| w-frame $f_2$ | 1 | 1 | 2 | 2 | 3 | 4 | | | | | | | | | | |

The example of $A_1$, since i=8 and j=6, has an alignment position 8, which is referred to as the start alignment position. In alignment $A_1$, the i-th number represents the position on the first string, and the j-th number represents the position on the second string. One counts only the letters (and not dashes). Accordingly, i=8 and j=6 represents alignment position 8. The w-frame $f_1$ starts from alignment position 8 and moves back 6 positions, as w=6. Therefore, $f_1(1)$ represents the alignment position 8, $f_1(6)$ represents alignment position 3. In general, $f_1(i)$ represents the alignment position 9−i. The value that a w-frame $f$ holds in $f(i)$ is the number of matches that occur between the start alignment position of that w-frame (denoted by s) and the alignment position s−i+1. This is illustrated in Table 5 below. This accumulated value of the matches is used for deciding whether a cell satisfies the third necessary condition.

TABLE 5

| Alignment $A_1$ | f | a | s | t | s | a | a | l | g | o | r | i | t | h | m | s |
| --- | --- | --- | --- | --- | --- | --- | --- | --- | --- | --- | --- | --- | --- | --- | --- | --- |
| | f | a | s | t | — | — | a | l | g | o | r | i | t | h | m | s |
| Position: | 1 | 2 | 3 | 4 | 5 | 6 | 7 | 8 | 9 | 0 | 1 | 2 | 3 | 4 | 5 | 6 |
| w-frame $f_1$ | 1 | 2 | 2 | 2 | 3 | 4 | | | | | | | | | | |
| Alignment $A_2$ | f | a | s | t | s | a | a | l | g | o | r | i | t | h | m | s |
| | f | a | s | t | — | a | — | l | g | o | r | i | t | h | m | s |
| Position | 1 | 2 | 3 | 4 | 5 | 6 | 7 | 8 | 9 | 0 | 1 | 2 | 3 | 4 | 5 | 6 |
| w-frame $f_2$ | 1 | 1 | 2 | 2 | 3 | 4 | | | | | | | | | | |

The operation shift captures the movement of the w-frame along the alignment. If the w-frame is moved one position to the right, then the operation of shift is performed on the old w-frame with the match-mismatch information of the new alignment position, to obtain a w-frame that correctly has information about the new alignment frame.

The operation merge is used to merge two w-frames. For example, $f=f_1+f_2$ for the previous example is $f$=1 2 2 2 3 4. By performing a merge operation, a w-frame $f$ has $f(i)$ values that contain the maximum number of matches in any one of the alignments that are considered during merging. Therefore, the new w-frame $f$ now has match-mismatch information about both alignments $A_1$ and $A_2$. Therefore, a w-frame can be used to make decisions taking into account all the alignments from a cell (i, j) as described below in further detail.

Dynamic Programming

The algorithm presented herein interleaves the feasibility and optimality steps described below. The algorithm ensures that no feasible solution is lost, and that no infeasible solutions are generated. The framework for solving the problem presented herein is dynamic programming.

The algorithm described herein follows the same framework. That is, this algorithm has the initialization step where the cells of the 0-th row and 0-th column are initialized, the dynamic programming computation of a general cell (i, j) and the traceback step where the optimal alignments are collected.

Optimal Alignment

A technique for finding optimal alignments that satisfy the (wh)-density constraint is now described. This technique uses the first, second and third necessary conditions described above, and the w-frame data structure. This technique uses the dynamic programming framework in a similar manner as used for the global alignment problem.

Initialization Step

Three steps (i) to (iii) presented in Table 6 below relate to initialization. For each cell, a value that represents the score for that cell is computed, $D_{i,j}$. $D_{i,j}$ is the alignment value at cell (i, j) that is being optimized, and $w_{i,j}$ is the w-frame at cell (i, j) that is used to make feasibility decisions.

TABLE 6

| | |
| --- | --- |
| (i) | (a) For cell (0, 0), define a w-frame $w_{0,0}$ such that $1 \leq k \leq w$, $w_{0,0}(k) = k$. |
| | (b) Let $D_{0,0} = 0$. |
| | (c) Mark cell (0,0) as feasible. |
| (ii) | For cell (0,j) such that $1 \leq j \leq w - h$, |
| | (a) Define a w-frame $w_{0,j}$ such that: $1 \leq k \leq j$, $w_{0,j}(k) = 0$ and $j + 1 \leq k \leq w$, $w_{0,j}(k) = k - j$ |
| | (b) Let $D_{0,j} = D_{0,j-1} + 1$. Establish a back pointer from $D_{0,j}$ to $D_{0,j-1}$. |
| | (c) Mark cell (0,j) as feasible. |

TABLE 6-continued (iii) For cell (i, 0) such that $1 \leq i \leq w - h$,
    (a) Define a w-frame $w_i,0$ such that $1 \leq k \leq i$, $w_{i,0}(k) = 0$ and
                             $i + 1 \leq k \leq w$, $w_{i,0}(k) = k - i$.
    (b) Let $D_{i,0} = D_{i-1,0}+1$. Establish a back pointer from
         $D_{i,0}$ to $D_{i-1,0}$.
    (c) Mark cell (0,i) as feasible.

Computation for a General Cell (i, j)

All cells (i, j) that are not processed in the initialization step are processed in the subsequent two steps: first, to determine the feasibility of the adjacent cells, and second, to perform the dynamic programming computations for the current cell. The initialization step encompasses the first and second conditions. The computation for the general cell encompasses the third condition. The final traceback step encompasses the last computations, which ensures the sufficiency criterion.

Feasibility Step

If a cell (i, j) does not satisfy the first necessary condition, then cell (i,j) is not considered further. No dynamic programming computation is done for the cell, and no back pointers are established. If a cell satisfies the first necessary condition, then let all adjacent cells having at least one back pointer established in them be called candidate cells. For each candidate cell c, let its w-frame already computed (in a previous dynamic programming step or in the initialization step) be denoted by $w_c$. Compute an intermediate w-frame for each candidate cell c, called $w_c'$ such that $w_c'=w_c$.shift(is Match( )), where is Match( ) function returns a value of 1 if moving from cell c to cell (i, j) is a match, otherwise the is Match( ) function returns a value of 0. Now, if, $w_c'(w) \geq h$, then mark candidate cell c as a feasible cell.

Dynamic Programming Computation Step

For a general cell (i, j) that has at least one feasible adjacent cell, the following computations are performed to compute the optimal alignment value $D_{i,j}$ for that cell. If the cell has no adjacent cells marked as feasible, then the cell is not considered for computation. No back pointers are established in that cell. $D_{i,j}$ is calculated according to Equation [3] below.

$$D_{i,j}=\min[(D_{i-1,j}+1)\cdot f(i-1,j), (D_{i,j-1}+1)\cdot f(i,j-1), (D_{i-1,j-1}+t(i,j))\cdot f(i-1,j-1)] \quad [3]$$

In Equation [3] above, function $f(p, q)$ returns a value of 1 if cell (p, q) is marked feasible, and function $t(p, q)$ returns an indication of infinity if $S_1(p)=S_2(q)$, otherwise the function $t(p, q)$ returns 1.

The computation of Equation [3] takes into account only those cells that have been marked as feasible according to the first and second necessary conditions, described above in relation to Equations [1] and [2]. This is due to the third necessary condition and is indicated by the function $f$. A mismatch is given a score of 1 and a match is given a score of 0. Therefore, the objective function is minimized. The minimum of the D-values computed from the adjacent feasible cells is assigned to the current cell. A back pointer is established from cell (i, j) to those adjacent feasible cells that have the minimum D-value as per Equation 131. Also, if more than one back pointer is established at cell (i, j), then each such back pointer is associated with the intermediate w-frame computed during the feasibility step. This w-frame associated with the back pointer is used in the traceback step described below.

The w-frame $w_{i,j}$ for cell (i, j) is computed as follows. Let $w_{i,j}$ be initialized to a w-frame with all zero values. For each adjacent feasible cell k to which a backpointer has been established, let the w-frame associated with the backpointer be $w_k$, update the current w-frame as $w_{i,j}=w_{i,j}+w_k$ where "+" represents the merge operation defined for w-frames.

Traceback Step

After the dynamic programming computations, if cell (n, m) has at least one back pointer established, then there is at least one solution. As in the case of normal global alignment problem, the optimal alignments can be collected by tracing the back pointers from cell (n, m) to cell (0, 0).

In the case of normal global alignment problem, any path taken from cell (n, m) to cell (0, 0) through the back pointers is a solution to the problem. In the case of the (wh)-density global alignment problem, however, not all paths through the back pointers from cell (n, m) to cell (0, 0) meet the specified (wh)-density constraint. Ensuring that the cells considered satisfy the third necessary condition ensures that from every cell that has a back pointer established, there is at least one path to (0, 0) that meets the density constraint. This does not mean, however, that all paths meet the density constraint. Therefore, at every point in the traceback, there are choices (to take multiple paths), so that one looks ahead to determine whether taking a path meets the density constraint. This is because of the third necessary condition that there is at least one choice that satisfies the density constraint, and hence there is no possibility of getting stuck and failing in the middle of tracing back. At every cell that has more than one back pointer, a "look ahead" is made to determine if one can take the path through a particular back pointer.

To do this, a w-frame is maintained for the path that is currently being traced through the back pointers. Let this w-frame be called w-current. Since the path back from cell (n, m) to cell (0, 0) is traced, unlike the forward computations, the w-frame w-current at a particular cell (i, j) holds information about the last w consecutive alignment positions from cell (i, j) to cell (n, m). At a cell with more than one back pointer, let the intermediate w-frame associated with back pointer "back" during the dynamic programming computation step be called w-back. The path through "back" can be safely taken if $\forall i$, $1 \leq i \leq w-1$, $w_{back}(i)+w_{current}(w-i) \geq h$. If the above condition is not satisfied, then taking the path through the back pointer "back" leads to an alignment that does not satisfy the (wh)-density constraint. All paths that reach cell (0, 0) by making decisions outlined above at each cell having more than one back pointer are solutions. The actual alignments for the paths can be obtained as for the normal global alignment case.

Computer Software

Computer software is used to programming the method described herein. An example algorithm is now described in pseudocode form in Table 7 below.

TABLE 7

Inputs are the two strings $S_1$ and $S_2$, and the two parameters w and h
1. Assign $w_{0,0}$ to cell(0,0) such that $1 \leq k \leq w$, $w_{0,0}(k)=k$. Assign $D_{0,0}=0$ to cell(0,0).
2. for each cell(0,j) such that $1 \leq j \leq w-h$
   a. Assign $w_{0,j}$ to cell(0,j) such that $1 \leq k \leq j$ $w_{0,j}(k)=0$ and $j+1 \leq k \leq w$ $w_{0,j}(k)=k-j$.
   b. Let $D_{0,j} = D_{0,j-1}+1$.
   c. Establish back pointer from $D_{0,j}$ to $D_{0,j-1}$
3. for each cell(i,0) such that $1 \leq i \leq w-h$
   a. Assign $w_{i,0}$ to cell(i,0) such that $1 \leq k \leq i$ $w_{i,0}(k)=0$ and $i+1 \leq k \leq w$ $w_{i,0}(k)=k-i$.
   b. Let $D_{i,0}=D_{i-1,0}+1$.
   c. Establish back pointer from $D_{i,0}$ to $D_{i-1,0}$.
4. for each cell(i,j) in the grid that has a back pointer established in it
   a. compute a new w-frame $w_{i,j}^{new}=w_{i,j}^{old}$.shift(isMatch( ))
   b. compute the $D_{i,j}$ value for the cell(i,j) as follows TABLE 7-continued $D_{i,j}=\min[(D_{i-1,j}+1), (D_{i,j-1}+1), (D_{i-1,j-1}+t(i,j))]$ where $t(p,q)$ returns 0 if $S_1(p)=S_2(q)$, otherwise it returns 1
   c. If $D_{i,j}=D_{i-1,j}$ establish a back pointer from cell(i,j) to cell(i-1,j)
If $D_{i,j}=D_{i,j-1}$ establish a back pointer from cell(i,j) to cell(i-1,j)
If $D_{i,j}=D_{i-1,j-1}$ establish a back pointer from cell(i,j) to cell(i-1,j-1)
  5. If cell(m,n) does not have a back pointer established, the problem has no solution. Exit with a no solution message.
  6. Set current cell as cell(m,n). Do until current cell is cell(0,0)
   a. Include current cell in the solution path.
   b. Choose an unmarked cell that is being pointed to by the current cell through a back pointer. If there is more than one back pointer, chose arbitrarily.
   c. Mark the chosen cell.
   d. Let w-frame of current cell be $w_{current}$, and that of the chosen cell be $w_{back}$.
   e. If for all i such that $1 \leq i \leq w-1$ $w_{back}(i)+w_{current}(w-i) \geq h$, let the chosen cell be the current cell. Jump to step 6a.
   f. Otherwise jump to step 6b.
  7. Output the solution path obtained in step 6 as one possible solution.
  8. Repeat step 6 for computing other solutions, until no more solutions can be found.

Computer Hardware

Figure 4:
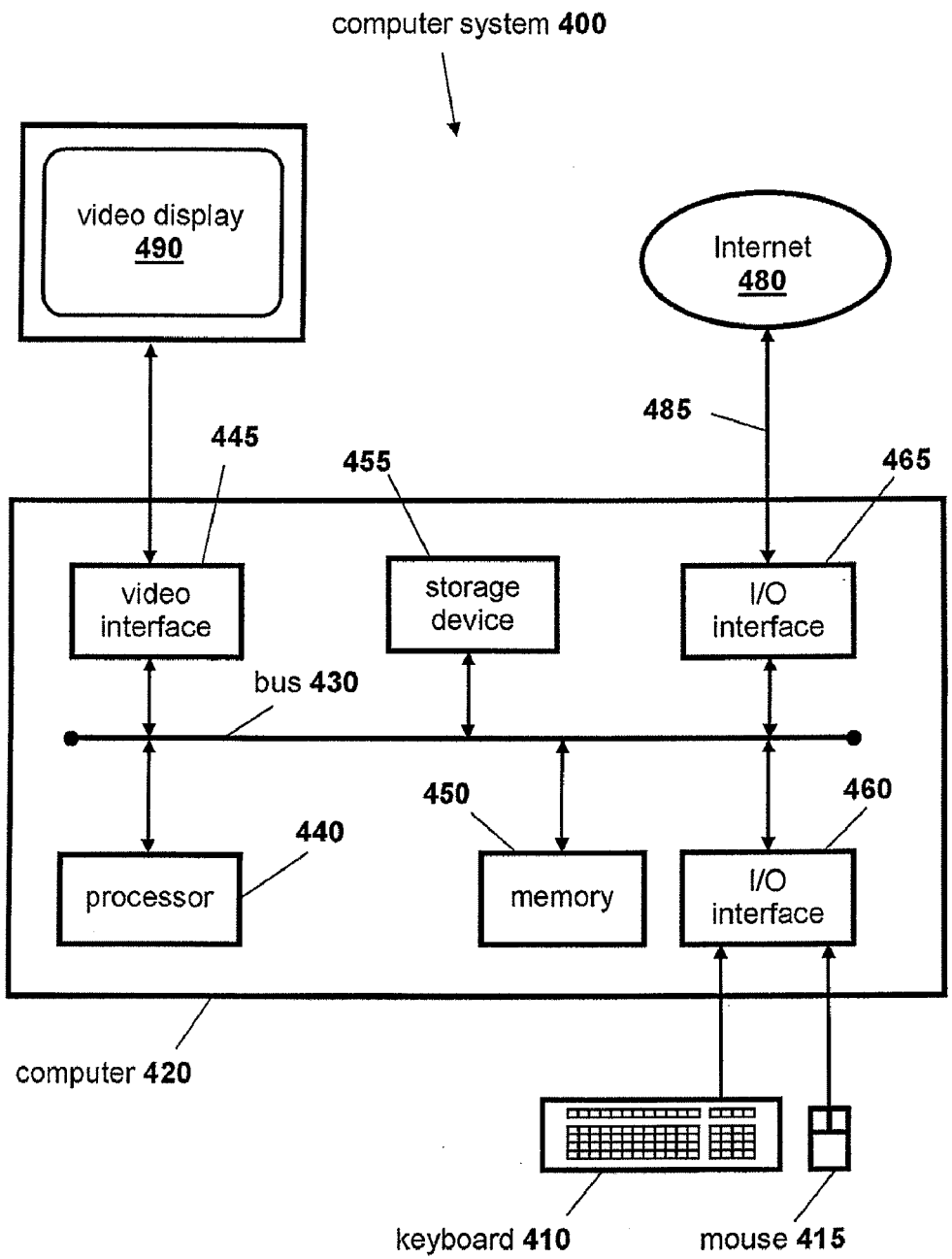
FIG. 4 is a schematic representation of a computer system suitable for performing the techniques described herein.

FIG. 4 is a schematic representation of a computer system 400 suitable for executing computer software programs. Computer software programs execute under a suitable operating system installed on the computer system 400, and may be thought of as a collection of software instructions for implementing particular steps.

The components of the computer system 400 include a computer 420, a keyboard 410 and mouse 415, and a video display 490. The computer 420 includes a processor 440, a memory 450, input/output (I/O) interfaces 460, 465, a video interface 445, and a storage device 455. All of these components are operatively coupled by a system bus 430 to allow particular components of the computer 420 to communicate with each other via the system bus 430.

The processor 440 is a central processing unit (CPU) that executes the operating system and the computer software program executing under the operating system. The memory 450 includes random access memory (RAM) and read-only memory (ROM), and is used under direction of the processor 440.

The video interface 445 is connected to video display 490 and provides video signals for display on the video display 490. User input to operate the computer 420 is provided from the keyboard 410 and mouse 415. The storage device 455 can include a disk drive or any other suitable storage medium.

The computer system 400 can be connected to one or more other similar computers via an input/output (I/O) interface 465 using a communication channel 485 to a network, represented as the Internet 480.

The computer software program may be recorded on a storage medium, such as the storage device 455. Alternatively, the computer software can be accessed directly from the Internet 480 by the computer 420. In either case, a user can interact with the computer system 400 using the keyboard 410 and mouse 415 to operate the computer software program executing on the computer 420. During operation, the software instructions of the computer software program are loaded to the memory 450 for execution by the processor 440.

Other configurations or types of computer systems can be equally well used to execute computer software that assists in implementing the techniques described herein.

Biological Applications

There are many applications relating to data representing sequences of molecular elements in molecular biology in which the number of allowed (or expected) differences between sets of molecular sequences is appropriately restricted. These problems typically arise in genomics, relating to DNA data rather than protein data. For a detailed survey and comparison of some of these applications and related considerations, refer to Chang, W. I. and Lampe, J., "Theoretical and empirical comparisons of approximate string matching algorithms", Proceedings of the 3rd Symposium on Combinatorial Pattern Matching, 1992, Springer LNCS 644, pages 175-84, which is hereby incorporated by reference in its entirety. A short summary of the applications of bounded difference problems in molecular biology is also presented in sections 12.2.1 and 12.2.2 of Gusfield, referenced above.

Nucleotide sequences, including polynucleotide and oligonucleotide sequences, include sequences of bases selected from adenine (A), thymine (T), cytosine (C) and guanine (G), which may be arranged in any order. A nucleotide sequence may encompass both coding regions (that is, regions resulting in gene expression), and non-coding regions.

Applications concerning sequence data of the type discussed in the above references include, but are not limited to, identifying the presence of nucleotide sequences of interest, such as coding sequences, regulatory sequences, promoter sequences, terminator sequences and the like, and identifying polymorphism or mutations. An allowed number of differences between sets of sequences may be selected so that coding regions can be matched when respectively interposed with non-coding regions. That is, alignment of sequence data for a pair of molecules may be determined as described herein, wherein a constraint of 70% homology is selected. That is, 70% homology requires, for the term hp/w described herein above, that h=0.7, where p is the length of the molecular sequence of the longer molecule in the pair, and w is some subsequence length, w<p. With these constraints, if the algorithm of Table 7 yields an alignment solution for a given frame size, i.e., subsequence length, w, then the molecular pair meets the 70% homology threshold for that alignment and the given frame size. The level of 70% homology is selected, for example, because this level may apply between sequences that have equivalent function, over a particular sequence length.

CONCLUSION

Various alterations and modifications can be made to the techniques and arrangements described herein, as would be apparent to one skilled in the relevant art.

What is claimed is:

1. A computer program product for execution by a computer system comprising computer hardware, the computer program product comprising a storage medium readable by the computer system and storing software instructions executable by the computer system for performing the following steps:
  receiving a first data string representing a first molecular sequence, with the first data string being a first sequence of characters;
  receiving a second data string representing a second molecular sequence, with the second data string being a second sequence of characters;
  determining a plurality of global alignments between the first data string and the second data string, with each global alignment representing a sequential correspondence between all of the respective characters of the first and second data strings, and where at least some of the plurality of global alignments include at least one non-character inserted into at least one of the first and second data strings;

providing a constraint value w to have an integer value greater than 1;
providing a constraint value h to have an integer value greater than 0 and less than w; and
determining the (wh)-density global alignment(s) from among the plurality of global alignments, with a (wh) density global alignment being defined as any alignment where for any w consecutive positions in the alignment there are at least h matches between the characters of the first and second data strings.

2. A computer program product for execution by a computer system comprising computer hardware, the computer program product comprising a storage medium readable by the computer system and storing software instructions executable by the computer system for performing the following steps:

receiving a first data string representing a first molecular sequence, with the first data string being a first sequence of characters;

receiving a second data string representing a second molecular sequence, with the second data string being a second sequence of characters;

determining a plurality of global alignments between the first data string and the second data string, with each global alignment representing a sequential correspondence between all of the respective characters of the first and second data strings, and where at least some of the plurality of global alignments include at least one non-character inserted into at least one of the first and second data strings;

providing a constraint value w to have an integer value greater than 1;
providing a constraint value h to have an integer value greater than 0 and less than w;
making a two-dimensional array of cells having the characters of the first data string along the first axis and the characters of the second data string along the second axis, where each cell is identified as cell (i,j), where i is a variable representing that cell's position along the first axis, where j is a variable representing that cell's along the second axis and where each global alignment can be represented as a sub-set of cells in the two-dimensional array;

determining a plurality of first-condition-meeting global alignments from among the plurality of global alignments with each first-condition-meeting global alignment can be represented as a first-condition-meeting subset of cells in the two-dimensional array, where a first-condition-meeting sub-set is defined as a sub-set where all cells of that sub-set meet the following condition:

$$\min(i,j) \geq \max(i,j) \cdot (h/w) \text{ when } \max(i,j) \geq w; \text{ and}$$

determining the (wh)-density global alignment(s) from among the plurality of first-condition-meeting global alignments, with a (wh) density global alignment being defined as any alignment where for any w consecutive positions in the alignment there are at least h matches between the characters of the first and second data strings.

* * * * *